US009298887B2

(12) United States Patent
Clark et al.

(10) Patent No.: US 9,298,887 B2
(45) Date of Patent: Mar. 29, 2016

(54) MEDICATION MANAGEMENT SYSTEM

(75) Inventors: Grant Thomas Clark, Baulkham Hills (AU); Paula Jane Clark, Baulkham Hills (AU)

(73) Assignee: White Cell Rx Holdings Pty Ltd, Baulkham Hills, New South Wales (AU)

( * ) Notice: Subject to any disclaimer, the term of this patent is extended or adjusted under 35 U.S.C. 154(b) by 154 days.

(21) Appl. No.: 14/128,507

(22) PCT Filed: Jul. 10, 2012

(86) PCT No.: PCT/AU2012/000827
§ 371 (c)(1),
(2), (4) Date: Mar. 5, 2014

(87) PCT Pub. No.: WO2013/006905
PCT Pub. Date: Jan. 17, 2013

(65) Prior Publication Data
US 2014/0340191 A1 Nov. 20, 2014

Related U.S. Application Data

(60) Provisional application No. 61/507,372, filed on Jul. 13, 2011.

(51) Int. Cl.
*G06F 19/00* (2011.01)
*G07F 17/00* (2006.01)
(Continued)

(52) U.S. Cl.
CPC ........ *G06F 19/3462* (2013.01); *G07C 9/00134* (2013.01); *G07F 17/0092* (2013.01); *A61J 7/0084* (2013.01)

(58) Field of Classification Search
CPC ... A61J 7/0076; A61J 7/0084; G06F 19/3456; G06F 19/3462
See application file for complete search history.

(56) References Cited

U.S. PATENT DOCUMENTS 6,601,729 B1 * 8/2003 Papp ............................... 221/25
2006/0058917 A1 * 3/2006 Vonk et al. .................... 700/236
(Continued)

FOREIGN PATENT DOCUMENTS

WO 99/60982 A2 12/1999
WO 2004/053620 A2 6/2004

OTHER PUBLICATIONS

International Search Report mailed Aug. 8, 2012 for Int'l Patent Application No. PCT/AU2012/000827, 5 pages.
(Continued)

*Primary Examiner* — Andrew Bee
(74) *Attorney, Agent, or Firm* — Kilpatrick Townsend & Stockton LLP

(57) ABSTRACT

A medication management system (100) for controlling access to medication. The system (100) comprises of a portable, electronically locking cassette (102) and a docking station (104). The cassette (102) comprises at least one internal compartment (110) adapted for storing patient-specific medication, a cover (114) adapted for restricting access to said compartment (110), a locking mechanism (112) for securing said cover (114), and means for storing a cassette identifier associated with said cassette. The docking station (104) comprises means for storing at least one authorized cassette identifier and at least one authorized user identifier, an input device (140) for receiving a user identifier, a cassette identifier, and a function identifier, and a controller (500B) for coupling said cassette (102) dependent upon said cassette identifier and said at least one authorized cassette identifier, validating a received user identifier and a received cassette identifier based upon said at least one authorized user identifier and said at least one authorized cassette identifier, operating said locking mechanism (112) based upon a received function identifier and said validation, and uncoupling said cassette (102) dependent upon said validation.

16 Claims, 9 Drawing Sheets

(51) Int. Cl.
*G07C 9/00* (2006.01)
*A61J 7/00* (2006.01)

(56) References Cited

U.S. PATENT DOCUMENTS

| | | |
|---|---|---|
| 2008/0319579 A1 | 12/2008 | Vahlberg et al. |
| 2009/0014458 A1 | 1/2009 | Heffron |
| 2009/0037020 A1 | 2/2009 | Brown |
| 2009/0108016 A1 | 4/2009 | Brown et al. |
| 2010/0096399 A1* | 4/2010 | Ratnakar .................... 221/1 |
| 2010/0256800 A1 | 10/2010 | Heffron |
| 2011/0166891 A1 | 7/2011 | Zerhusen et al. |

OTHER PUBLICATIONS

International Preliminary Report on Patentability mailed Feb. 25, 2013 for Int'l Patent Application No. PCT/AU2012/000827, 14 pages.

Office Action (English Translation) mailed Jun. 17, 2015 in Chinese Patent Application No. 201280034630X, 4 pages.

Extended European Search Report mailed Feb. 6, 2015 in European Patent Application No. 12811684.5, 12 pages.

* cited by examiner

MEDICATION MANAGEMENT SYSTEM

CROSS-REFERENCE TO RELATED APPLICATIONS

This application is the National Phase of International Application No. PCT/AU2012/000827, filed Jul. 10, 2012, which claims priority to U.S. Provisional Application No. 61/507,372, filed Jul. 13, 2011, the disclosures of which are hereby incorporated by reference in their entirety for all purposes.

TECHNICAL FIELD

The present invention relates generally to a system of medical apparatus and, in particular, to an electronic medication management system for controlling access to medication.

BACKGROUND

The health system is under increasing pressure from a growing and ageing population, and an increase in chronic diseases. A study by Deloitte Touche Tohmatsu, entitled *National E-Health and Information Principal Committee: National E-Health Strategy* dated September 2008 on page 9, states that the hospital system in Australia is made up of more than 1,320 public and private hospitals, admitting around 19,000 patients per day, and providing non-admitting services to another 125,000 patients daily. Another study by the Australian Department of Health and Ageing, entitled *The State of Our Public Hospitals—June* 2010 Report, states that this equates to nearly 5 million admissions annually to public hospitals, and another 3.5 million patients annually to private hospitals.

In a Victoria State Government audit conducted by the Victorian Auditor General, entitled *Patient Safety in Public Hospitals* dated May 2008, medical error was found to have occurred in 10% of patients admitted to a public hospital in Victoria with an estimated cost of $511 million annually. A study by The Joanna Briggs Institute, entitled *Best Practice Information Sheet: Strategies to reduce medication errors with reference to older adults*, in vol 9, Issue 4, dated 2005, states that nationally, it is estimated that medication errors alone cost approximately $350 million annually.

Medication errors have various consequences. Some patients experience little or no effect, some have temporary or permanent injury, and in a small percentage of cases, the outcome is fatal. The vast majority of medication errors are avoidable.

In the quest for solutions to these avoidable mistakes with potentially catastrophic outcomes, there has been much research around the world into the causes and effects of medication errors. The causes are multifaceted due in large part to the number of individuals involved in each stage of the medication administration process. Thus, there is no one-dimensional solution.

Traditionally, the process of medication management has been paper-based, such as handwritten notes, prescriptions, record keeping and incident reporting. Unfortunately, the traditional method provides little opportunity for a detailed analysis of medication errors. The traditional method is especially vulnerable to compound errors as handwritten communications are read and re-written in each stage of the medication administration process. Examples of these errors are typographical errors, misreading and the like. In addition, there are further human errors due to fatigue or memory lapses.

Therefore, a need exists to provide a medication management system that provides clear and consistent communications, and allows medical staff to double check medication at each stage of the medication administration process.

SUMMARY

According to an aspect of the present disclosure, there is provided a system for controlling access to medication, the system comprising: a portable, electronically locking cassette for securing medication, said cassette comprising: a housing having at least one internal compartment adapted for storing the patient-specific medication; a cover adapted for restricting access to said compartment; a locking mechanism for securing said housing and cover together in a closed position when locked; and means for storing a cassette identifier associated with said cassette; and a docking station adapted for coupling with said cassette, said docking station comprising: means for storing at least one authorised cassette identifier and at least one authorised user identifier; an input device for receiving a user identifier, a cassette identifier, and a function identifier; and a controller for: coupling said cassette dependent upon said cassette identifier and said at least one authorised cassette identifier; validating a received user identifier and a received cassette identifier based upon said at least one authorised user identifier and said at least one authorised cassette identifier; operating said locking mechanism based upon a received function identifier and said validation; and uncoupling said cassette dependent upon said validation.

BRIEF DESCRIPTION OF THE DRAWINGS

Embodiments of the present invention are described hereinafter with reference to the drawings, in which.

DETAILED DESCRIPTION

The medication management system is a system for controlling access to medication stored in portable cassettes. The cassettes are typically locked and docked at docking stations located in various sites throughout a premises; in which the system is implemented. Typically, the system is implemented in a medical facility, and an admitted patient is assigned to a cassette and a docking station.

The cassette stores medication specific to a patient, and can only be accessed by an authorized medical staff member. The docking station provides a secure housing for the cassette, and is usually proximate to the patient's bedside for ease of access. Besides providing a secure housing, the docking station typically serves as the sole communications vehicle to access the cassette and also ensures the location of the cassette is easily trackable. To administer the medication or to modify the medication in the cassette, an authorized medical staff member enters identifiers (e.g., authorization codes) which unlock and uncouple the cassette from the docking station to allow access to the stored medication. The docking station associated with the cassette may also contain an electronic inventory system for tracking the medication quantity inside the associated cassette, which increases the accuracy of the medication being administered to a patient.

Figure 1:
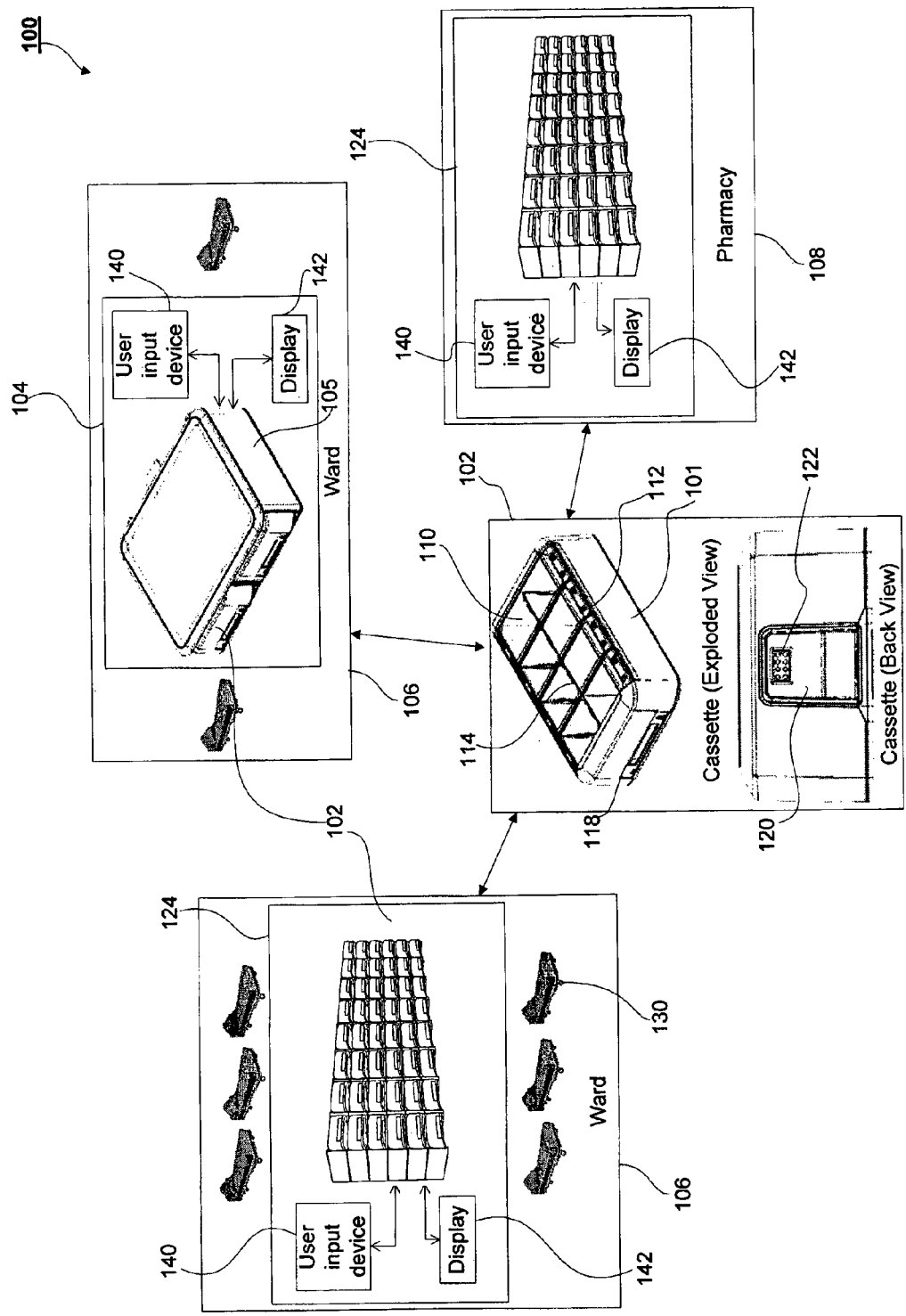
FIG. 1 shows a medication management system according to an embodiment of the present invention.

FIG. 1 illustrates an embodiment depicting a high level view of the medication management system 100 comprising a portable, electronically locking cassette 102 for securing medication specific to a patient and a docking station 104 adapted for coupling with the cassette 102.

The cassette 102 comprises a housing 101 having at least one internal compartment 110 adapted for storing medication, a cover 114 adapted for restricting access to said compartment 110, a locking mechanism 112 for securing said housing 101 and cover 114 together in a closed position when locked, and a digital recording medium for storing a cassette identifier associated with said cassette 102. The cassette identifier is discussed hereinafter. The digital recording medium can be implemented using any of a number of technologies adapted for storing such a cassette identifier. The digital recording medium may be a Read-Only Memory (ROM), Random Access Memory (RAM), flash memory, magnetic storage media such as a hard disk drive (HDD), optical media including CD-ROM, DVD, and Blu-Ray, barcode, a watermarked indicia where the watermark encodes the cassette identifier in the indicia, and phase change memory.

The housing 101 may be made out of metals or plastics, and may be moulded to integrate the internal compartment 110. Alternatively, the internal compartment 110 may be a separate container inserted into the housing 101.

In FIG. 1, the cassette 102 is depicted to have a plurality of internal compartments 110. The internal compartments 110 are inaccessible when the cover 114 is closed and locked by the locking mechanism 112.

The cover 114 may be made out of metals or plastics, and may also be partly or wholly transparent to allow a medical staff member to inspect the content of the cassette 102.

The locking mechanism 112 may comprise an electronic latch or an electromagnetic lock (e.g., a solenoid lock) that is operable by a controller 500B (e.g., a microprocessor) of the docking station 104. The controller 500B of the docking station 104 unlocks the locking mechanism 112 based upon validation of received identifiers from the user input device 140, which is a part of the docking station 104 and is described hereinafter. The locking mechanism 112 typically cannot be unlocked when the cassette 102 is uncoupled from a docking station 104. The controller 500B of the docking station 104 is described in detail in relation to FIG. 5B.

The cassette 102 is typically a reusable, portable container (i.e., size of 0.001 m³ to 0.2 m³) that can be easily transported by a medical staff member from the pharmacy 108 to the ward 106, or from the docking stations 104, 124 to a patient's bedside.

As shown in FIG. 1, the cassette 102 further includes a display 118, a coupling port 120 for coupling to docking stations 104, 124, and a communications interface 122 for communicating with a docking station 104.

The display 118 may be a liquid crystal display (LCD) panel, LED lights or the like that may display, inter alia, one or more of the following:

the name of the patient associated with the cassette 102,
the medication stored in the cassette 102,
the inventory level of the cassette 102,
the identifiers received from user input device 140, and
any alerts that need attentions of medical staffs.

The coupling port 120 allows the cassette 102 to couple to a docking station 104, 124. Coupling of the cassette 102 to a docking station 104, 124 may be done via an electromagnetic lock (e.g., solenoid lock), an electronic latch, or a combination of both. The electromagnetic lock or the electronic latch is typically located at a coupling port of the docking station 104, described hereinafter, whilst the coupling port 120 generally contains the passive complementary component.

The communications interface 122 allows the cassette 102 to communicate with the docking station 104, which in turn allows a medical staff member to program the cassette 102 (i.e., to associate the cassette 102 to a patient). A cassette 102 can only communicate with the coupled docking station 104.

The other component of the medication management system 100 is the docking station 104. The docking station 104, 124 comprising a digital recording medium for storing at least one authorised cassette identifier and at least one authorised user identifier; an input device 140 for receiving a user identifier, a cassette identifier, and a function identifier; and a controller 500B. The controller 500B is used for coupling the cassette 102 dependent upon the cassette identifier and the at least one authorised cassette identifier; validating a received user identifier and a received cassette identifier based upon the at least one authorised user identifier and the at least one authorised cassette identifier; operating the locking mechanism 112 based upon a received function identifier and the validation; and uncoupling the cassette 102 dependent upon the validation. The identifiers are discussed hereinafter. The digital recording medium may be a Read-Only Memory (ROM), Random Access Memory (RAM), flash memory, magnetic storage media such as a hard disk drive (HDD), optical media including CD-ROM, DVD, and Blu-Ray, barcode, a watermarked indicia where the watermark encodes the cassette identifier in the indicia, and phase change memory.

The docking station 124 is a cluster of docking stations capable of storing a number of cassettes 102, as shown in FIG. 1. The cluster docking station 124 may be used in wards 106 to service several patients or a pharmacy 108 where a large amount of cassettes 102 are stored awaiting refill. On the other hand, the docking station 104 is a dual docking station capable of only storing two cassettes 102, as depicted in FIG. 1. The dual docking station 104 may be used in wards 106 as an alternative to the cluster docking station 124, and is usually located beside a patient's bed 130. The dual docking station 104 may be used to serve a patient whereby the patient has two cassettes 102 assigned to the patient. Hereinafter, docking stations of any configurations are collectively assigned the reference numeral 104.

The docking station 104, as described hereinbefore, includes a user input device 140. The user input device 140 is typically formed by keys (not shown), a keypad (not shown) or like controls. In some implementations, the user input devices 140 may include a touch sensitive panel (not shown) physically associated with the display 142 to collectively form a touch-screen. Such a touch-screen may thus operate as one form of graphical user interface (GUI) as opposed to a prompt or menu driven GUI typically used with keypad-display combinations. Other forms of user input devices may also be used, such as a swipe card reader (not illustrated) or a barcode reader (not illustrated).

The user input device 140 receives identifiers from a medical staff member, which are validated against authorized identifiers stored in the docking station 104. The identifiers and corresponding matters are discussed in detail hereinafter.

If the received identifiers are valid, the docking station 104 subsequently sends a control signal to the docked cassette 102 to unlock the locking mechanism 112 and uncouple the cassette 102 from the docking station 104 effectively allowing access to the internal compartment 110. The identifiers increase the accuracy of administering the medication to the correct patient.

The only method of accessing the cassette 102 is by entering the identifiers into the user input device 140, which is typically located next to a docking station 104 for ease of access. In larger wards 106, the user input device 140 may also be located at a central location. When a medical staff member accesses a central user input device, the accessed cassette 102 and docking station 104 provide a signal (e.g., a blinking light) to notify the medical staff member the location of the accessed cassette 102 and the accessed docking station 104.

As mentioned hereinbefore, the docking station 104 may contain an electronic inventory system for tracking the quantity of medication inside the cassette. The user input device 140 provides access to the inventory system for updating and checking the medication stored in the associated cassette 102. Typically, the inventory system is updated after medication is added into or removed from the cassette 102. A log of all entries to the user input device 140 is also maintained for monitoring purposes.

Other inventory systems for tracking the quantity of medication may be used. Such inventory system may include a paper-based or an electronic list located proximate to the docking station 104.

The identifiers mentioned above are identification codes that are associated with, inter alia, medical staff (authorized user identifier), cassettes 102 (cassette identifier), medication (medication identifier), docking stations 104, 124 (docking station identifier), or actions to be performed (function identifiers). The identification codes may exist in the form of barcodes, digital codes stored in cards, magnetic stripes, or passwords.

Function identifiers are identifications that associate a function to be performed by medical staffs when accessing the cassette 102. Function identifiers may also control the steps to be taken upon release of the associated cassette 102 and upon coupling of cassette 102 to the associated docking station 104. An example is illustrated hereinafter.

Cassette identifiers are identifications associated with the cassette, and may also include information associated with a patient (patient identifier) or information associated with a medication (medication identifier). Hereinafter, the identifiers are typically in the form of digital codes that are stored in the memory of devices (e.g., cassettes 102, docking stations 104, 124) and can be entered into the devices through a user input device 140.

For example, the cassette 102 or the docking stations 104, 124 store authorized identifiers in a memory of the respective devices to be used to validate identifiers received from user input device 140.

For example, a medical staff member enters an authorized user identifier, a cassette identifier (with an incorporated patient identifier) and a function identifier. In this example, the entered authorized user identifier is "Alan Jones", the cassette identifier is "1234-y001" and the function identifier is "administer med". The docking station 104 verifies whether "Alan Jones" is allowed access and/or has sufficient access to the corresponding cassette 102 to perform the required "administer med" function identifier. The docking station 104 also verifies whether the cassette identifier, which in this example is composed of two parts "1234" identifying the cassette and "y001" identifying the patient associated with the cassette 102, is correct. If all received identifiers are correct, the docking station 104, unlocks the associated cassette's locking mechanism 112 and uncouples the cassette 102. Otherwise, an alarm is activated and the cassette 102 stays locked and docked at the docking station 104. The alarm may be audible or an LED light sequence.

In an example regarding the function identifier, the docking station 104 utilises the function identifiers to determine whether to unlock the cassette 102 upon release. For example, if the medical staff enters a "refill" function identifier, the docking station 104 releases the cassette 102 but does not unlock the cassette 102 because, typically, the cassette 102 is only refilled in the pharmacy 108. If the medical staff member wants to refill the cassette 102 in the ward 106, then the medical staff member must enter the correct function identifier into the user input device 140 to unlock the cassette 102. For example, a function identifier of "refill at ward" may be specified as a valid function. On the other hand, if the medical staff enters an "administer" function identifier, the docking station 104 releases and unlocks the corresponding cassette 102 in parallel, which allows access to the internal compartment 110.

Upon completion of medication administration or refill, the medical staff member closes the cover 114, which automatically engages locking mechanism 112 and locks the cover 114 in place. The medical staff member then proceeds to couple the cassette 102 to the associated docking station 104, and updates the inventory system. If the medical staff member does not update the inventory system, an alarm may be activated to alert the medical staff member to update the inventory system. As mentioned hereinbefore, a function identifier also has a corresponding expected inventory update, and if the inventory update is not as expected, an alarm may be activated.

For example, a "refill" function identifier has an expected increase in inventory. If the inventory update results in a decrease of inventory, an alarm may be activated. Conversely, an "administration" function identifier has an expected decrease in inventory by a certain amount of medication. If the inventory update results in an increase or an unexpected decrease, an alarm may be activated. A medical staff member may have to enter a notation on why the inventory update is different than expected. Thus, the inventory update provides an opportunity to attend to a medication error shortly after the error occurs.

When a medical staff member administers medication, the person typically carries a medication administration list having information of medication for each patient and the administration time. The medication administration list may be displayed on handheld devices (e.g., iPad, PDA, mobile phone), mobile computer devices (e.g., laptop, computer carts, etc), or the like. Alternatively, the medication administration list may be located at a patient's bedside and is displayed on an electronic display (e.g., LCD screen), which is continuously updated by a centralised hospital system. The displays 118, 142 allow the medical staff member to cross check the information displayed on displays 118, 142 with the information on the medication administration list.

Typically, the docking station 104 includes a mounting for mounting on a fixed structure. Examples of fixed structures are walls, portable or permanent stands, or the beds 130. The portable or permanent stands may be stands having components for the docking station 104 to mount. The portable stand may be used for a medical facility with a shortage of docking stations 104. Thus, the portable stand can be placed on a location which a docking station 104 is needed. Alternatively, permanent stands may be implemented on locations and docking stations 104 may be moved from location to location depending on needs. Typically, the fixed structure is proximate to a bed for ease of access.

The docking station 104 also includes a communications interface (not shown) for communicating with a cassette 102 for coupling and programming purposes (e.g., to associate the cassette 102 to a patient) and with the medical facility's server computer for programming purposes (e.g., to associate the docking station 104 to a patient). The docking station 104 may only communicate with a cassette 102 when the cassette 102 is coupled to the docking station 104 or the cassette 102 is in the process of coupling to the docking station 104. The process of coupling a cassette 102 to a docking station 104 is described in detail in relation to FIG. 7.

Further, the docking station 104 includes an enclosure 105, coupling ports (not shown) for coupling to cassettes 102, and a display 142. As depicted in FIG. 1, the docking station 104 comprises an enclosure 105 adapted for housing cassettes 102, which increases security to the cassette 102.

The coupling port of the docking station 104 allows a cassette 102 to couple to the docking station 104 upon validation of the aforementioned identifiers. Typically, the docking station coupling port comprises at least of an electromagnetic lock that latches to a complementary component in the cassette 102. The electromagnetic lock is typically a solenoid, which becomes an electromagnet when electric current passes through the solenoid. The complementary component in the cassette 102 may be a metal plate for magnetically attaching to the electromagnetic lock. Other coupling mechanism that may be used are, inter alia, a latch or a fastener that may latch or fasten to a suitable complementary component at the cassette 102.

The communications interface of the docking station 104 allows the docking station 104 to communicate with the cassette 102. The communications interfaces of the cassette 102 and the docking station 104 may communicate with each other via a wired or wireless connection.

The display 142 has the same functionality as the cassette display 118.

As mentioned hereinbefore, the cassette 102 may only communicate with and through the coupled docking station 104. Thus, a manual override feature is implemented in the event of a system or power failure. The manual override may be a manual lock on each of the cassette 102 and the docking station 104. A complementary key, if used on the respective manual locks, allows a medical staff member to unlock cassette 102 or uncouple a cassette 102 from a docking station 104.

Figure 2:
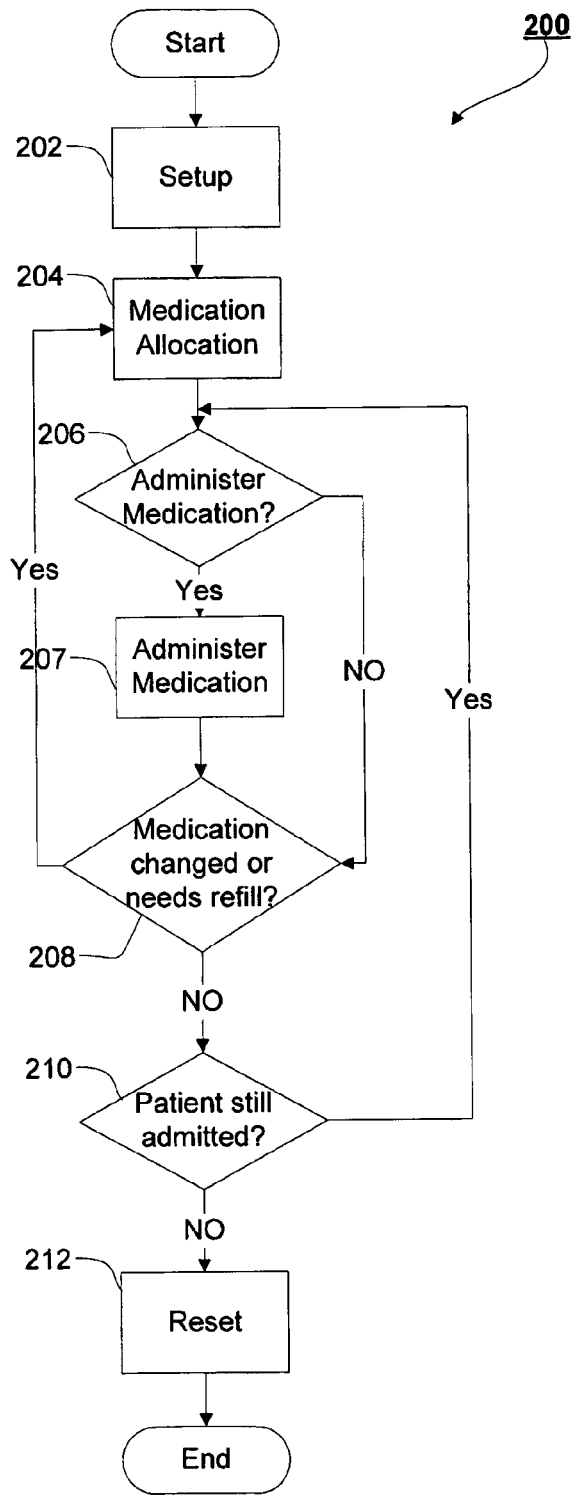
FIG. 2 is a flow diagram of an operational method of the system shown in FIG. 1.

FIG. 2 shows a flow diagram for a method 200 depicting a typical operation of the system 100. The method 200 commences with setup step 202 where a cassette 102 and a docking station 104 are assigned to a patient, upon admission of the patient to a medical facility (e.g., hospital, aged care facility). However, the system 100 may also be implemented in, inter alia, a retail pharmacy, a medication warehouse, and a domestic premises. In these other premises, the cassette 102 may be associated with specific medication instead of a specific patient.

For example, in a hospital, the cassette identifier may include the cassette's serial number and the patient identifier associated with the cassette 102. However, in a warehouse, the cassette identifier may include the cassette's serial number and the medication identifier associated with the cassette 102.

The patient may be assigned a docking station 104 that is nearby to the patient's allocated bed 130. In this step, identifiers capable of accessing the assigned cassette 102 and the assigned docking station 104 are also specified.

For example, when a patient is admitted, a medical staff member (e.g., a nurse, a doctor) in the hospital allots a bed 130 to a patient. For ease of operation, the bed 130 may already have an associated docking station 104 which is automatically assigned to the patient. The docking station 104 may also have an authorization level already established, allowing nurses and doctors having the required level of authorization to access the docking station 104 and the corresponding cassette 102.

An unallocated cassette 102, which is located in a bay of docking stations 104 storing unallocated cassettes 102, is allocated to the admitted patient. To assign an unallocated cassette 102 and docking stations 104 to a patient, an authorized medical staff member programs the cassette 102 and the docking station 104 via the user input device 140. Alternatively, if the cassette 102 and docking station 104 are embedded within a centralised hospital system, the hospital server can automatically program the assignment. The newly assigned cassette 102 is transferred and docked to the corresponding docking station 104. During the assignment process, tags or labels may also be placed on the cassette 102 identifying the associated patient and medication for reducing the chance of the medication being administered incorrectly.

Alternatively, a cassette 102 may already be associated with a docking station 104 and is already coupled to the docking station 104 on a constant basis. In this case, a pair of docking station 104 and cassette 102 is assigned automatically to a patient upon allocating a bed 130 to the patient either by a medical staff member or, as described above, by a central hospital server.

Processing advances from step 202 to step 204 upon completion of the setup process.

In step 204, the cassette 102 receives a medication allocation from a doctor. If system 100 is not integrated into a hospital system, a nurse receives the medication allocation notice via a handwritten note or the like. The nurse then accesses the corresponding docked cassette 102 by entering the required identifiers into the user input device 140, which effectively uncouples the cassette 102 from the corresponding docking station 104 and transports the cassette 102 to the pharmacy 108. The process of a medical staff member uncoupling and transporting a cassette 102 is described hereinafter in relation to FIG. 8.

On the other hand, if the system 100 is integrated into a hospital system having a server computer and a communication network, the medication allocation may be transmitted to the corresponding cassette 102 by the server computer via the associated docking station 104. In this case, a signal is displayed on both displays 118, 142 notifying medical staffs that the docked cassette 102 needs to be filled with medication. In turn, a medical staff member enters the required identifiers into the user input device 140 to uncouple the cassette 102 from the docking station 104, and transports the uncoupled, locked cassette 102 to the pharmacy 108.

While awaiting refill, the cassette 102 may be docked in a docking station 104 of the pharmacy 108 or be placed undocked in a secure area. To obtain access to the internal compartment 110 of a cassette 102, a pharmacist enters identifiers into the docking station's user input device 140 to unlock the cassette 102 and to undock the cassette 102 from the docking station 104 at the same time. Alternatively, if the cassette 102 is undocked, a pharmacist docks the cassette 102 to an interim docking station 104 and enters identifiers into the interim docking station 104. Upon validation of identifiers, the interim docking station 104 unlocks and undocks the cassette 102. The pharmacist fills the cassette 102 with the required medication, locks the cassette 102, and docks the cassette 102 to an interim docking station 104 to update the inventory of the cassette 102. By entering the identifiers and updating the inventory of the cassette 102, there is an increased level of accuracy of medication stored in the cassette 102. Upon filling the cassette 102, the cassette 102 is returned to the associated docking station 104 in ward 106. Step 204 advances to decision step 206.

In the decision step 206, the system 100 checks for any action to administer medication to the patient. If the system 100 does not receive any action to administer medication to a patient (No), processing continues to step 208. Conversely, if system 100 receives an action to administer medication to a patient (Yes), processing advances from step 206 to step 207.

In step 207, medication is administered to the patient by an authorized medical staff member. Upon administration of medication, the medical staff member updates the inventory system of the cassette 102, which presents an opportunity for the medical staff member to double check that the correct medication has been administered. A more detailed description of this step is illustrated in relation to FIG. 8. Processing continues at step 208.

In decision step 208, the system 100 checks if the cassette 102 needs refilling or there has been a change in medication. Typically, cassette 102 has a minimum quantity of the medication, which is usually programmed during the initial medication allocation of step 204, which triggers an alert that the cassette 102 needs refilling. If there is a change in medication or a refilling event to be performed (Yes), processing continues at step 204. Otherwise (No), processing continues from step 208 to step 210.

Decision 210 checks (verifies) if the patient associated with the cassette 102 is still admitted at the hospital. If the patient is still admitted (Yes), processing continues at step 206. Otherwise (No), processing advances to step 212.

In step 212, the docking station 104 and the cassette 102 are reset. Processing then ends.

Figure 3:
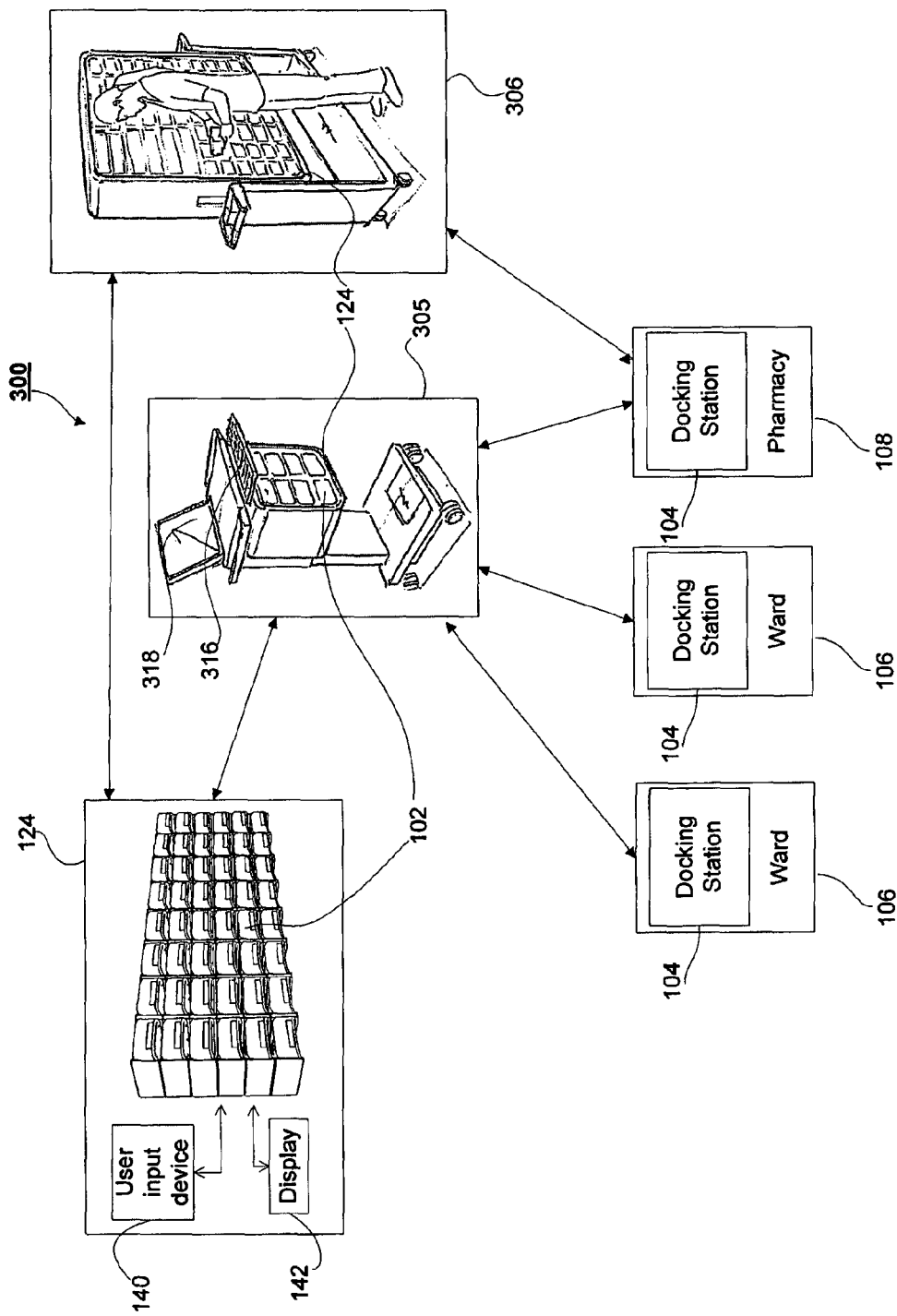
FIG. 3 shows another embodiment of the medication management system.

FIG. 3 illustrates a system 300 in accordance with an alternative embodiment. The system 300 comprises the same components of the system 100 of FIG. 1 and further includes a mobile cart 305 and a supply cart 306. Components of system 100 that are the same in FIG. 3 as in FIG. 1 use the same reference numbers as used in FIG. 1. The mobile cart 305 and the supply cart 306 include at least one docking station 104 to provide access to a cassette 102 and secure transportation for cassettes 102.

Typically, the docking station 104 includes a mounting for mounting on a mobile cart 305. The mounting to the mobile cart 305 may be temporary or permanent. The mobile cart 305 typically includes shelves (not shown) to secure the locked cassettes 102.

The mobile cart 305 and the supply cart 306 include a user input device 316 (not shown on supply cart 306), a display 318 (not shown on supply cart 306), and a docking station 104. Functionalities of these components are the same as the functionalities of docking station 104 described hereinbefore. In other words, the mobile cart 305 and the supply cart 306 are transportable docking stations.

Cassettes 102 may be stored in a centralised docking station 104. If medications are to be administered to patients, a medical staff member moves the corresponding cassettes 102 to a docking station 104 of the mobile cart 305. The medical staff member then conveys the mobile cart 305 to a ward 106. Upon reaching the patient's bedside, the medical staff member enters the required identifiers into the user input device 316 and the appropriate cassette 102 is released from the docking station 104 and is also unlocked in parallel. Upon conclusion of medication administration, the medical staff member updates the inventory system, locks the cassette 102 by closing the cover 114 and secures the cassette 102 to the mobile cart 305.

On the other hand, if the mobile cart 305 only has shelves for transporting locked cassettes 102 and one docking station 104, a medical staff member loads the locked cassettes 102 to the shelves for transportation to patients' bedsides. Upon reaching a patient's bedside, the medical staff member checks the medication administration list with the information displayed on a locked cassette display 118. The cassette 102 with corresponding information is coupled to the one docking station 104 of the mobile cart 305, and the medical staff member enters identifiers to the user input device 316. If the identifiers are valid, the cassette 102 is unlocked and undocked from the docking station 104. Upon completion of the medication administration, the medical staff member locks and couples the cassette 102 to the mobile cart docking station 104 to update the inventory system. The medical staff member proceeds to enter identifiers to uncouple the locked cassette 102 and store the locked cassette 102 on the shelves of the mobile cart 305. The medical staff member repeats the process for the next patient.

If a medication for a cassette 102 is to be modified, similar step to step 204 of method 200 is performed. In this case, a medical staff member may use a supply cart 306 for transporting cassettes 102 to pharmacy 108. Upon completion of refill or medication administration, cassettes 102 are returned to their corresponding centralised docking station 104 using the mobile cart 305 or the supply cart 306.

Figure 4:
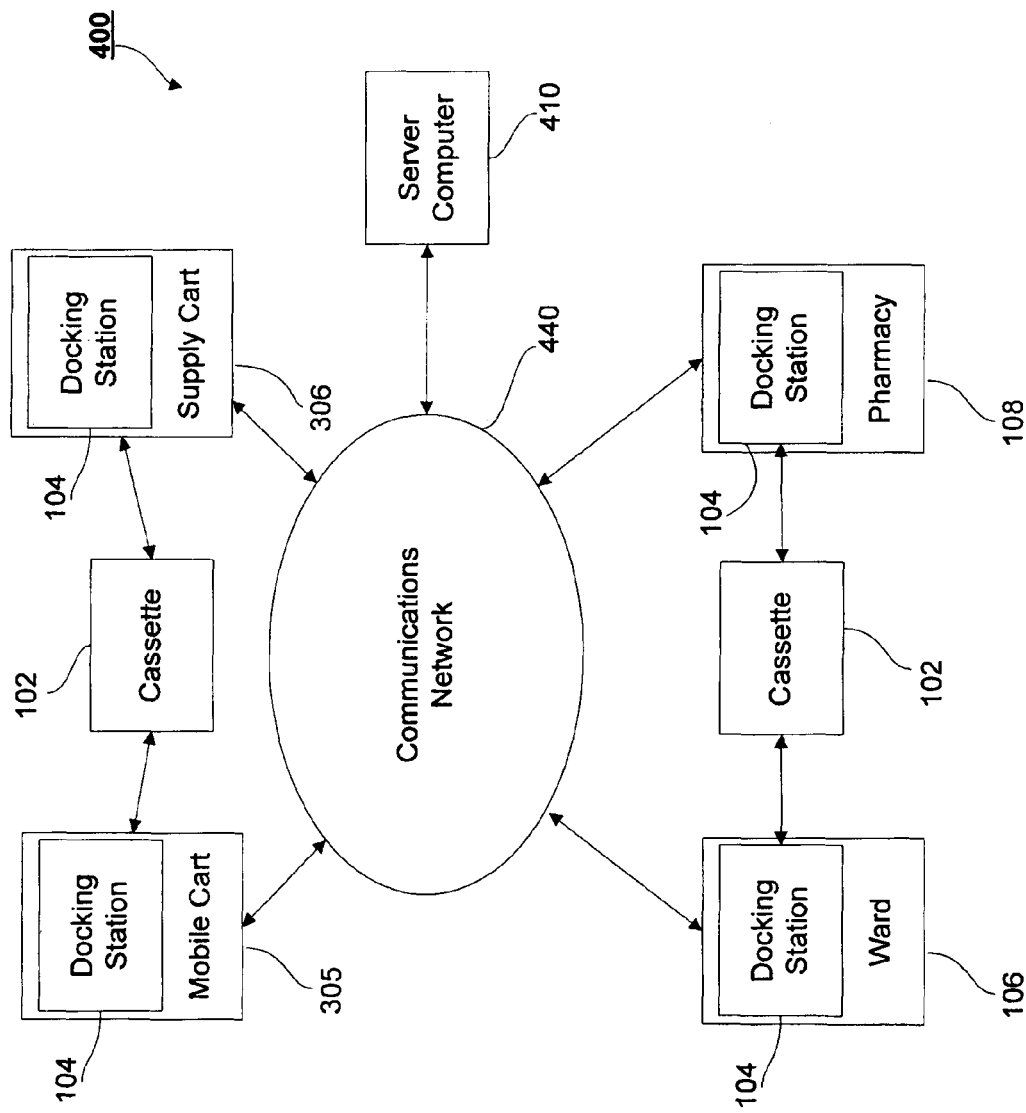
FIG. 4 illustrates the medication management system controlled or aided in operation by a server computer.

FIG. 4 is a representation of the medication management system 400 controlled or aided in operation by a server computer 410. In this configuration, the server computer 410 communicates to docking stations 104 via a communications network 440. The server computer 410 may perform some or all of the application programs of the docking station 104.

In an example, the server computer 410 may communicate with the docking stations 104 for associating a patient with a pair of cassette 102 and docking station 104 during the setup step 202 of method 200.

In a further example, when a docking station 104 receives identifiers on the user input device 140, the docking station 104 transmits the received codes to the server computer 410 via the communications network 440. The server computer 410 processes the received identifiers and sends a signal to the docking station 104 whether to allow access to the medical staff member based upon validation of the received identifiers with the server's stored identifiers.

Figure 5A:
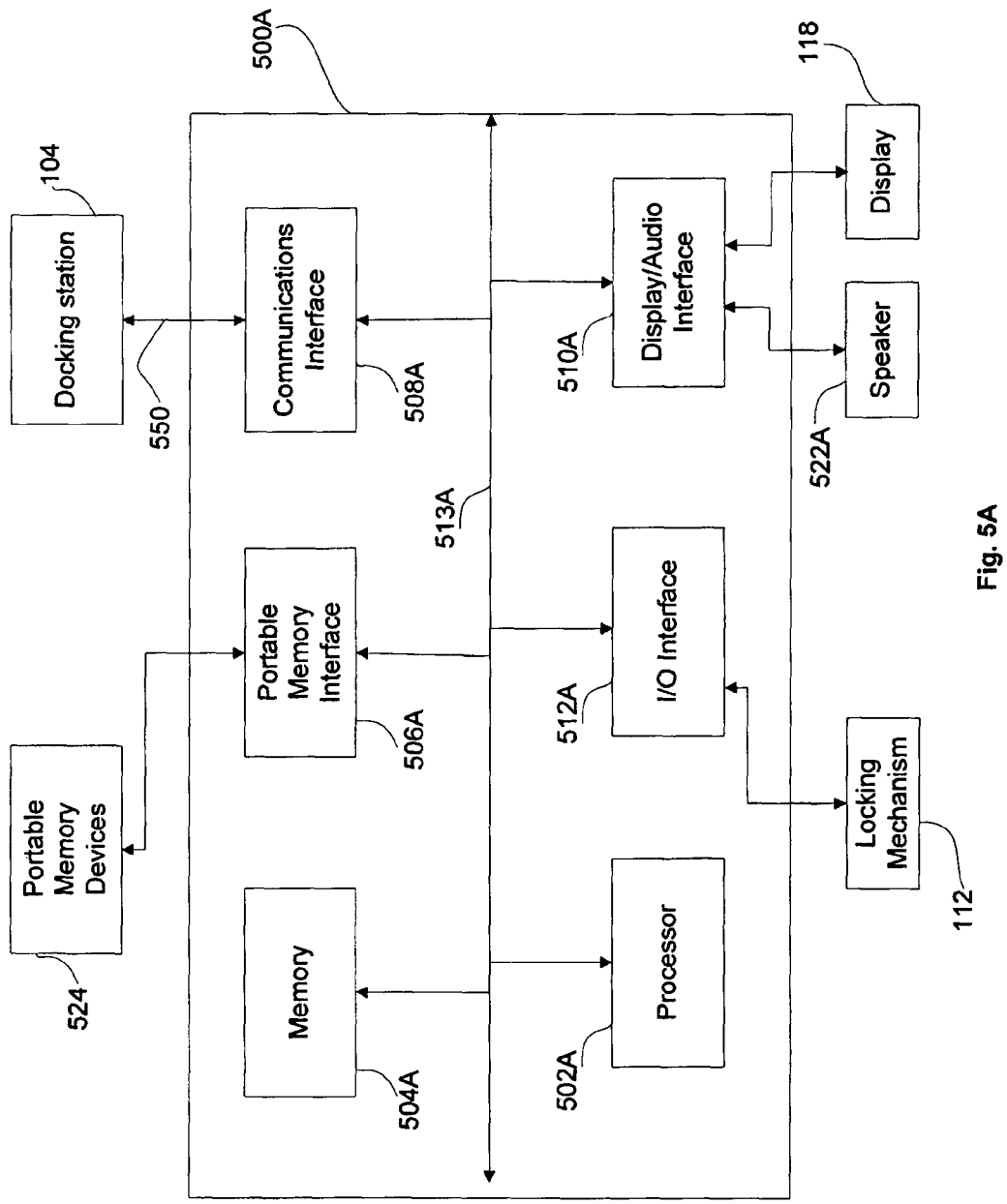
FIG. 5A is the controller of the cassette.

FIG. 5A shows a schematic block diagram of the controller 500A of the cassette 102. The controller 500A comprises a processor 502A which is bi-directionally coupled via an interconnected bus 513A to a memory 504A, a portable memory interface 506A, a communications interface 508A, a display/audio interface 510A, and an I/O Interface 512A. Typically, the controller 500A includes a battery to supply power to the cassette 102.

Typically the processor 502A has an on-board memory. Memory 504A is coupled to processor 502A as additional memory. The on-board memory of processor 502A and memory 504A may be formed from non-volatile semi-conductor read only memory (ROM), semi-conductor random access memory (RAM) and possibly a hard disk drive (HDD). The RAM may be volatile, non-volatile or a combination of volatile and non-volatile memory.

Alternatively, the controller 500A may exclude a processor 502A. In this case, the controller 500A is only capable of receiving control signals from the coupled docking station 104 from the communications interface 508A via connection 550. In other words, controller 500B of the docking station 104 controls the operation of controller 500A.

The memory 504A stores cassette identifiers that may contain information associated with a patient assigned to the cassette or information associated with a medication of the patient assigned to the cassette.

The display/audio interface 510A is connected to the display 118. The display interface 510A is configured for displaying information on the display 118 in accordance with instructions received from processor 502A, to which the display interface 510A is connected.

The display/audio interface 510A is also connected to the speaker 522A, which generates sounds in accordance with instructions received from processor 502A. For example, the speaker 522A generates an alarm when an unauthorized user tries to gain access to a cassette 102.

The communications interface 508A allows a cassette 102 to communicate with a docking station 104. For example, the connection 550 may be radio frequency or optical. An example of a wired connection includes Ethernet. Further, an example of wireless connection includes Bluetooth™ type local interconnection, Wi-Fi (including protocols based on the standards of the IEEE 802.11 family), Infrared Data Association (IrDa) and the like.

Figure 5B:
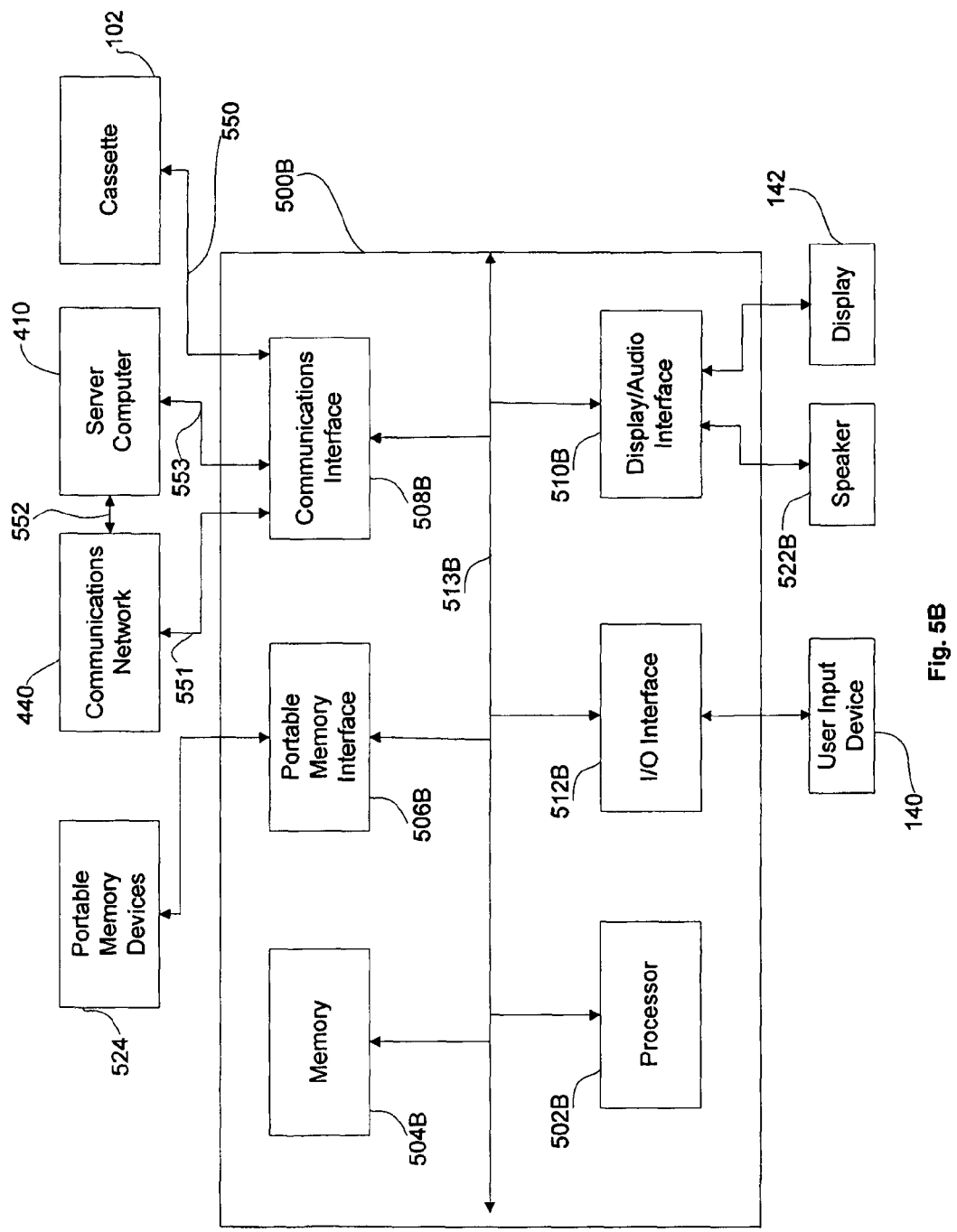
FIG. 5B is the controller of the docking station.

FIG. 5B shows a schematic block diagram of the controller 500B of the docking station 104. The controller 500B also comprises a processor 502B which is bi-directionally coupled via an interconnected bus 513B to a memory 504B, a portable memory interface 506B, a communications interface 508B, a display/audio interface 510B, and an I/O Interface 512B.

The memory 504B stores authorized identifiers that are allowed access to the docking station 104 and subsequently the associated cassette 102. The memory 504B also stores inventory of corresponding cassettes 102 and a log recording all received identifiers and inventory updates.

The portable memory interface 506B allows a complementary portable memory device 524 to be coupled to the docking station 104 to act as a source or destination of data. Examples of such interfaces permit coupling with portable memory devices such as Universal Serial Bus (USB) memory devices, Secure Digital (SD) cards, Personal Computer Memory Card International Association (PCMIA) cards, optical disks and magnetic disks. These portable memory devices 524 may be used to load application programs, default settings, information associated with a patient or a medication, and information associated with cassettes 102 that are allowed to dock on a docking station 104.

The docking station 104 has a communications interface 508B to permit coupling of the docking station 104 directly to a server computer 410 via connection 553 or alternatively via a communications network 440 via connection 551 to a server computer 410 via connection 552. The connections 551, 552, 553 may be wired or wireless. Examples of the wired and wireless connection have been discussed in relation to the communications interface 508A.

The display/audio interface 510B is connected to display 142 and speaker 522B. The display 142 displays, inter alia, status of cassette 102 and historical data of accesses by medical staff members. Similar to speaker 522A, the speaker 522B also generates an alarm when an unauthorized medical staff member tries to uncouple a cassette 102 from a docking station 104.

For example, to unlock and undock a cassette 102 from a docking station 104, a nurse or a doctor enters identifiers into the user input device 140, which is transmitted to the processor 502B. The processor 502B in turn communicates with memory 504B to obtain the identifiers associated with the cassette 102. The processor 502B then proceeds to validate the received identifiers against the stored identifiers in memory 504B. If the received identifiers are valid, the processor 502B sends an unlock signal to the associated cassette 102 via the communications interface 508B to the communications interface 508A via connection 550. The control signal is in turn transmitted to the locking mechanism 112 via the I/O interface 512A. The locking mechanism 112 contains a driver (not shown) to control the locking and unlocking operation. Conversely, if the received identifiers are invalid, the processor 502B sends a signal to speaker 522B and display 142 via the display/audio interface 510B to generate an alarm. The alarm signal may also be sent to the corresponding cassette speaker 522A and display 118 via the communications interface 508B via the connection 550 via the communications interface 508A and finally via the display/audio interface 510A.

Hereinafter, controllers 502A and 502B are collectively referred to as reference numeral 502. Memories 504A and 504B are collectively referred to as reference numeral 504. Speakers 522A and 522B are collectively referred to as reference numeral 522.

Figure 6:
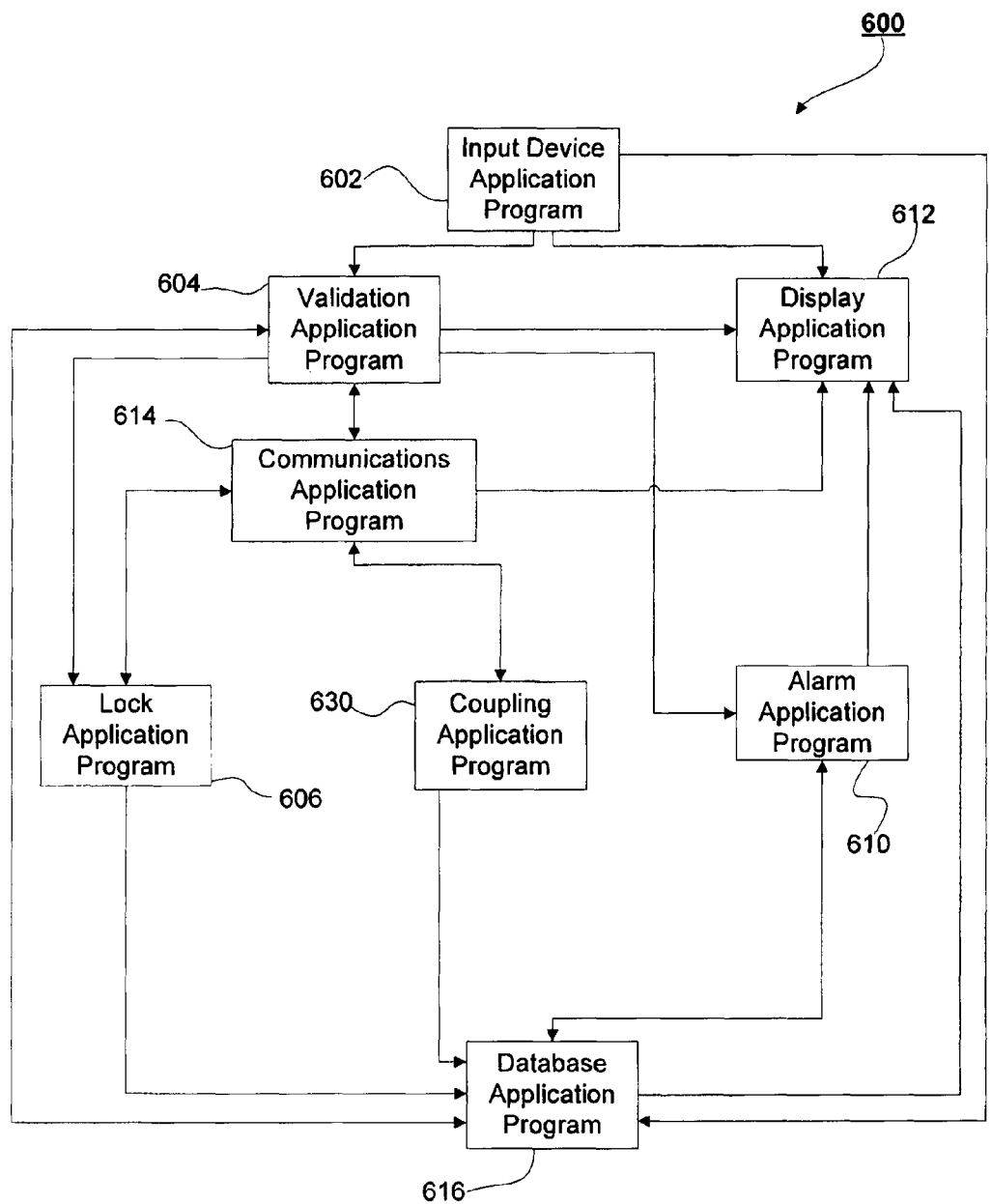
FIG. 6 is a software architecture for the system.

FIG. 6 is a representation of the software architecture 600 to operate the cassette 102 and the docking station 104. The software architecture comprises of an input device application program 602, a validation application program 604, a lock application program 606, a coupling application program 630, an alarm application program 610, a display application program 612, a communications application program 614, a database application program 616. Typically, all of these application programs are installed on the docking station 104. If the processor 502A exists in controller 500A, the lock application program 606, the alarm application program 610, the display application program 612, and the communications application program 614 are installed on the cassette 102 and executed by the processor 502A to control operation of the locking mechanism 112, the speaker 522A, the display 118 and the communications interface 508A, respectively. Alternatively, some of the application programs may be installed on and executed by the server computer 410.

Hereinafter, the application programs are assumed to be installed on and executed by the docking station 104.

The input device application program 602 is a code module capable of receiving inputs (e.g., identifiers, updates of inventory) from the user input devices 140. When the input is an identifier, the input device application program 602 sends the received identifiers to the validation application program 604 for validation. Alternatively, when the input is an update to the inventory, the input device application program 602 sends the received update to the database application program 616 for updating the database. The database application program 616 is discussed further hereinafter.

The validation application program 604 communicates with the database application program 616 to compare the received identifiers with stored identifiers. The stored identifiers are managed by the database application program 616. The database application program 616 is discussed in more detail hereinafter.

If the received identifiers are valid, the validation application program 604 subsequently produces a control signal to the lock application program 606, which in turn unlocks the locking mechanism 112 of cassette 102 by conveying the control signal to the cassette 102 by using the communications application program 614. The lock application program 606 logs unlock/lock events into the database application program 616 for records purposes. However, when the received identifiers are invalid, the validation application program 604 produces a control signal to the alarm application program 610, which triggers an alarm. The alarm may be an alarm sound generated by speaker 522 and/or a blinking light. The alarm application program 610 logs alarm events into the database application program 616 for records purposes.

The validation application program 604 utilizes the communications application program 614 for communicating with the server computer 410, if the system 400 is implemented.

When identifiers are received, the input device application program 602 also communicates with the display application program 612, in parallel, to display the received data.

The display application program 612 is a code module for displaying information on the displays 118, 140, 318 the respective devices 102, 104, 305. Besides displaying inputs or identifiers received at the user input device 140, the display application program 612 also displays alarms generated by the alarm application program 610, validation results from the validation application program 604, communications status from the communications application program 614, and stored identifiers of the database application program 616. Other information that may be displayed has been described hereinbefore.

The communications application program 614 is a code module that manages communications between the docking station 104, the cassette 102, and the server computer 410, if the system 400 is implemented.

The database application program 616 manages the database of the docking station 104 and the server computer 410. The database may contain, inter alia, the inventory of a cassette 102, identifiers associated with the cassette 102 or the docking station 104, and the corresponding cassette 102 that may dock on a docking station 104. The database application program 616 communicates with the alarm application program 610 to generate an alarm when an unexpected inventory update occurs or an expected inventory update does not occur or when inventory level of cassette 102 is below a minimum threshold.

The coupling application program 630 is a code module for controlling the coupling mechanism of a docking station 104 for coupling a cassette 102 to the docking station 104. The coupling application program 630 is connected to the database application program 616 for verifying that an inserted cassette 102 is allowed to dock at a docking station 104. The coupling application program 630 is further connected to the communications application program 606 for communicating with an inserted cassette 102 (e.g., to receive cassette identifiers). The methods described hereinafter may be implemented using the controller 502. The processes of FIGS. 7 and 8 may be implemented as one or more software application programs 602 to 630 stored in memory 504 and executable within the processor 502. The docking station 104 of FIGS. 1, 3 and 4 implement the described methods. Alternatively, the server computer 410 may implement some or all of the steps of the described methods. The software instructions may be formed as one or more code modules, each for performing one or more particular tasks.

Figure 7:
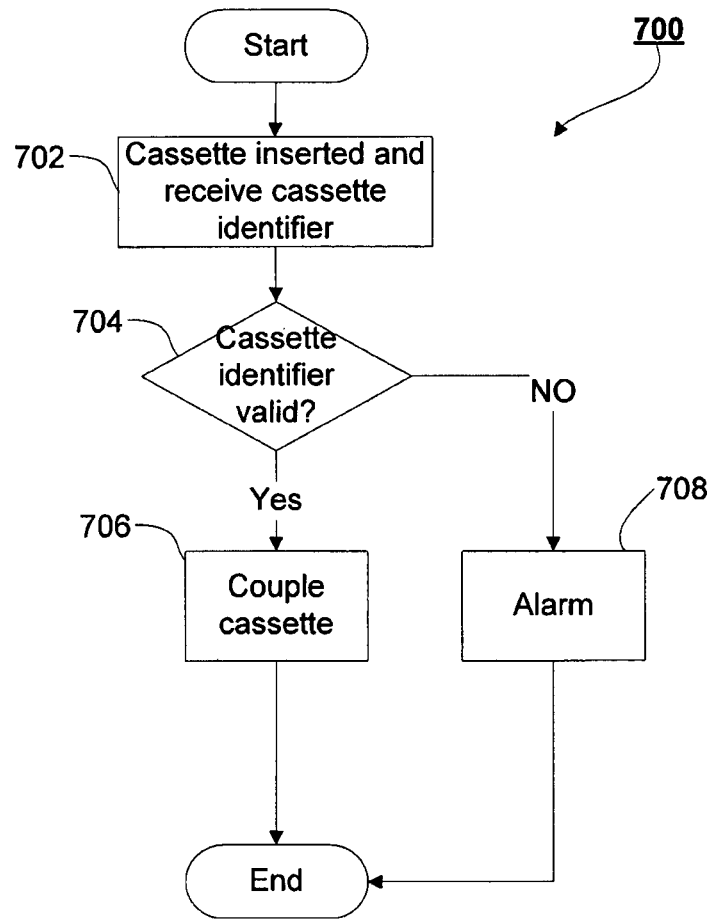
FIG. 7 is a flow diagram of a method for coupling the cassette to the docking station.

FIG. 7 is a flow diagram of a method 700 performing a coupling between a cassette 102 and a docking station 104. Method 700 commences at step 702 where a docking station 104 receives identifiers from a cassette 102 being inserted into the docking station 104. Firstly, the docking station 104 identifies that a cassette 102 is engaging the docking station port (not shown). For example, the identification may occur through a spring button, located at the docking station 104, which is depressed when a cassette 102 is inserted and advances the method 700 to the next step.

When an event of a cassette 102 being inserted into a docking station 104 is identified, the coupling application program 630 of the docking station 104 requests the cassette identifier from the inserted cassette 102 by using the communications application program 614. As described above, the cassette identifier includes information associated with the cassette 102 and may also include information of the associated patient and/or the associated medication. In turn, the coupling application program 630 receives the cassette identifier of the inserted cassette 102 via the communications application program 614. Step 702 advances to step 704.

In decision step 704, the docking station 104 checks the received cassette identifier is valid. The validation occurs by authenticating the received cassette identifier with the stored cassette identifier in the docking station 104, as previously described. If the received cassette identifier is valid (Yes), method 700 moves to step 706.

In step 706, the coupling application program 630 sends a signal to the coupling port 120 to couple the cassette 102 to the docking station 104. The locking mechanism 112 contains a driver (not shown) which subsequently maintains an electric current through the solenoid in docking station 104 and engages the metal plate in cassette 102. Processing then ends.

On the other hand, if the received cassette identifier is invalid (No) in step 704, method 700 moves to step 708, which triggers an alarm notifying that the cassette 102 does not belong in the docking station 104. The method 700 then ends.

Figure 8:
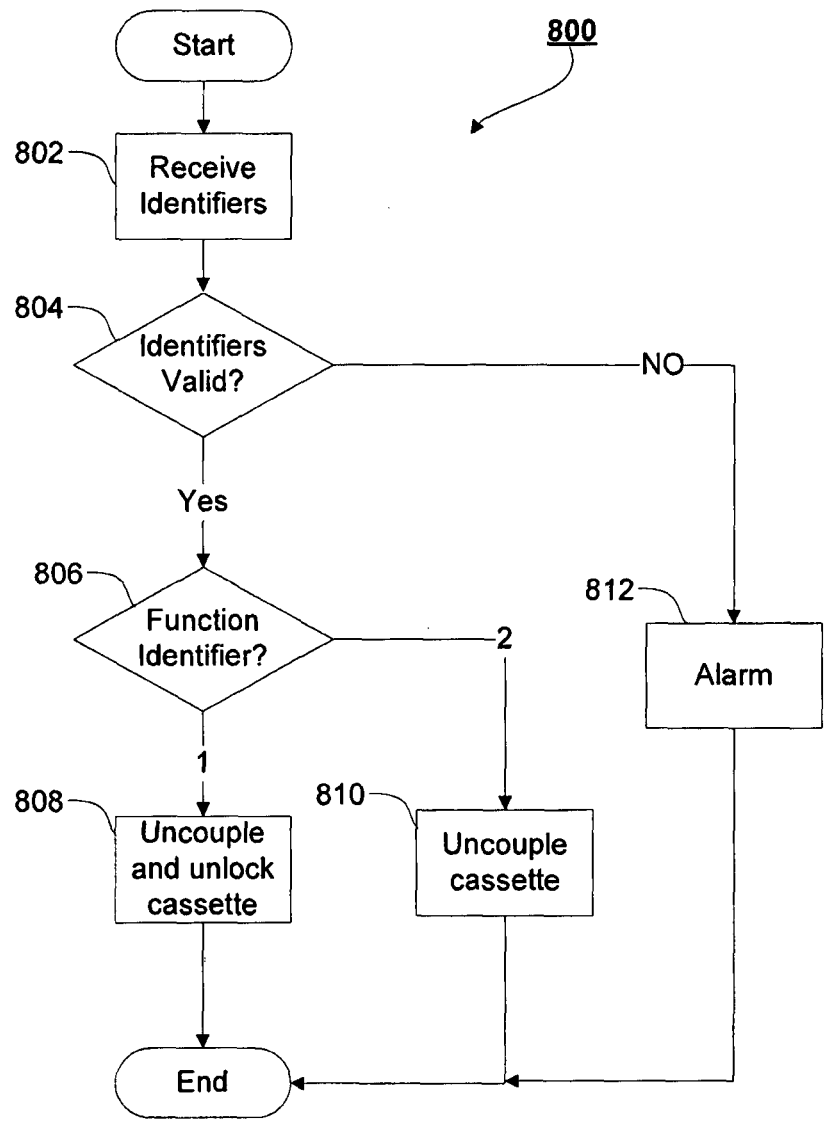
FIG. 8 is a flow diagram of a method for uncoupling the cassette from the docking station.

FIG. 8 is a flow diagram of method 800 representing the process of uncoupling a cassette 102 from a docking station 104 for filling/refilling the cassette 102 or for administering medication of cassette 102 to a patient. Method 800 starts at step 802.

In step 802, a user input device 140 receives identifiers which are handled by the input device application program 602, which is similar to a previously described method of receiving identifiers. Method 800 advances to step 804.

In decision step 804, the validation application program 604 validates the received identifiers against the stored identifiers of docking station 104, which has been described previously. When all the received identifiers are valid, method 800 advances to step 806.

In the decision step 806, the validation application program 604 checks if the function identifier is received. If the received function identifier relates to a first code (1), method 800 advances to step 808. On the other hand, if the received function identifier relates to a second code (2), method 800 advances to step 810.

For example, a first code of the function identifier is to administer medication to a patient, whilst a second code of the function identifier is to refill/change medication of the cassette 102.

In step 808, the coupling application program 630 uncouples the cassette 102 corresponding to the received cassette identifier, and the lock application program 606 unlocks the corresponding cassette 102. Processing then ends.

In step 810, the coupling application program 630 uncouples the cassette 102 but the lock application program 606 does not unlock the corresponding cassette 102. Processing then ends.

For example, a medical staff member enters identifiers including the medical staff identification code, the patient identifier, and the function identifier. Firstly, the docking station 104 confirms that the medical staff identification code has sufficient authorization level to access the docking station 104. Secondly, the docking station 104 confirms that the corresponding cassette 102, which is associated with the received patient identifier, resides at the docking station 104. Thirdly, the received function identifier is analysed to determine whether to unlock cassette 102. In this example, the stored function identifier includes "administer medication" and "fill/refill cassette". Upon confirmation of the identifiers, the docking station 104 releases the corresponding cassette 102 and unlocks cassette 102 if the received function identifier is "administer medication". Otherwise, the corresponding cassette 102 is released but stays locked.

If at step 804 the validation application program 604 determines that one of the identifiers is invalid (No), method 800 advances to step 812, which triggers an alarm as executed by the alarm application program 610.

Method 800 concludes at the completion of step 808, 810 or 812.

In operation, the medication management system 100 provides consistent and clear communications to medical staffs at each stage of the medication process, which potentially would reduce the amount of medication errors. Further, the management system 100 also prompts the medical staffs to at least double check the medication being administered to a patient, which further reduces the chance of an error occurring.

INDUSTRIAL APPLICABILITY

The arrangements described are applicable to the medical industry and particularly for hospitals and other medical facilities where medications are being handled regularly.

The foregoing describes only some embodiments of the present invention, and modifications and/or changes can be made thereto without departing from the scope and spirit of the invention, the embodiments being illustrative and not restrictive.

The invention claimed is:

1. A system for controlling access to medication, the system comprising:
   a portable, electronically locking cassette for securing medication specific to a patient, said cassette comprising:
   a housing having at least one internal compartment adapted for storing the patient-specific medication;
   a cover adapted for restricting access to said compartment;
   a locking mechanism for securing said housing and cover together in a closed position when locked; and
   a digital recording medium for storing a cassette identifier associated with said cassette, the cassette identifier having a patient identifier associated with said patient; and
   a docking station adapted for coupling with said cassette, said docking station comprising:
   a digital recording medium for storing at least one authorized cassette identifier and at least one authorized user identifier, the at least one authorized cassette identifier having an authorized patient identifier associated with said patient;
   an input device for receiving a user identifier, a cassette identifier including a patient identifier, and a function identifier that associates a function to be performed when the cassette is being accessed; and
   a controller for:
   controlling said docking station to allow said cassette, to be coupled to said docking station, depending on a first validation of a received cassette identifier including the patient identifier against said at least one authorized cassette identifier including the authorized patient identifier;
   controlling said docking station to allow said cassette to be uncoupled from said docking station depending on a second validation of a received user identifier and the received cassette identifier based upon said at least one authorized user identifier and said at least one authorized cassette identifier; and
   operating said locking mechanism based upon a received function identifier and the second validation.

2. The system according to claim 1, wherein said cover is made out of metal or plastic.

3. The system according to claim 1, wherein said cover is transparent.

4. The system according to claim 1, wherein:
   said cassette further comprises a communications interface; and
   said docking station further comprises a communications interface for communicating with said cassette communications interface via a wired or a wireless connection.

5. The system according to claim 1, wherein said system is implemented in one of the following premises:
   a medical facility;
   an aged care facility;
   a retail pharmacy;
   a medication warehouse; and
   a domestic premises.

6. The system according to claim 1, wherein the cassette identifier comprises information associated with a medication.

7. The system according to claim 1, wherein said docking station further comprises a mounting for mounting on a fixed structure.

8. The system according to claim 7, wherein said fixed structure is proximate to a bed.

9. The system according to claim 1, wherein said docking station further comprises a mounting for mounting on a mobile cart.

10. The system according to claim 1, wherein said locking mechanism comprises an electromagnetic lock.

11. The system according to claim 1, wherein said cassette is reusable.

12. The system according to claim 1, wherein said docking station further comprises an enclosure adapted for housing said cassette.

13. The system according to claim 1, wherein said docking station further comprises an electromagnetic lock for coupling said cassette to said docking station.

14. The system according to claim 1, wherein said docking station digital recording medium further comprises an inventory system for tracking the quantity of medication inside said cassette.

15. The system according to claim 14, wherein said input device is adapted for updating said inventory system.

16. A method for unlocking the portable, electronically locking cassette of the system of claim 1, said method comprising:

receiving a user identifier, a cassette identifier including a patient identifier, and a function identifier in the input device of the docking station, the function identifier being associated with a function to be performed when the cassette is being accessed;

controlling said docking station to allow said cassette to be uncoupled from the docking station depending on the first validation of the received cassette identifier including the patient identifier against said at least one authorised cassette identifier including the authorised patient identifier; and operating said locking mechanism based upon the received function identifier and the second validation of the received user identifier and the received cassette identifier based upon said at least one authorised user identifier and said at least one authorised cassette identifier.

* * * * *